United States Patent [19]
Thal

[11] Patent Number: 5,891,168
[45] Date of Patent: Apr. 6, 1999

[54] PROCESS FOR ATTACHING TISSUE TO BONE USING A CAPTURED-LOOP KNOTLESS SUTURE ANCHOR ASSEMBLY

[76] Inventor: Raymond Thal, 11321 Bright Pond La., Reston, Va. 22094

[21] Appl. No.: 942,544

[22] Filed: Oct. 1, 1997

Related U.S. Application Data

[63] Continuation-in-part of Ser. No. 792,738, Jan. 31, 1997, Pat. No. 5,709,708.

[51] Int. Cl.$^6$ .................................................. A61B 17/04
[52] U.S. Cl. ........................... 606/232; 606/139; 606/224
[58] Field of Search .................................... 606/232, 139, 606/72, 75, 78, 219, 224

[56] References Cited

U.S. PATENT DOCUMENTS

| | | |
|---|---|---|
| 4,007,743 | 2/1977 | Blake . |
| 4,532,926 | 8/1985 | O'Holla . |
| 4,537,185 | 8/1985 | Stednitz . |
| 4,632,101 | 12/1986 | Freedland . |
| 4,721,103 | 1/1988 | Freedland . |
| 4,870,957 | 10/1989 | Goble et al. . |
| 4,898,156 | 2/1990 | Gatturna et al. . |
| 4,946,468 | 8/1990 | Li . |
| 5,013,316 | 5/1991 | Goble et al. . |
| 5,037,422 | 8/1991 | Hayhurst et al. . |
| 5,084,050 | 1/1992 | Draenert . |
| 5,102,421 | 4/1992 | Anspach, Jr. ............................ 606/232 |
| 5,141,520 | 8/1992 | Goble et al. ............................ 606/232 |
| 5,192,303 | 3/1993 | Gatturna et al. ....................... 606/232 |
| 5,207,679 | 5/1993 | Li ............................................ 606/232 |
| 5,224,946 | 7/1993 | Hayhurst et al. ....................... 606/232 |
| 5,236,445 | 8/1993 | Hayhurst et al. ....................... 606/232 |
| 5,258,016 | 11/1993 | DiPoto et al. .......................... 606/232 |
| 5,356,413 | 10/1994 | Martins et al. . |
| 5,358,511 | 10/1994 | Gatturna et al. . |
| 5,370,661 | 12/1994 | Branch . |
| 5,370,662 | 12/1994 | Stone et al. ............................ 606/232 |
| 5,372,146 | 12/1994 | Branch . |
| 5,372,599 | 12/1994 | Martins . |
| 5,383,905 | 1/1995 | Golds et al. . |
| 5,400,805 | 3/1995 | Warren . |

*Primary Examiner*—Gary Jackson
*Attorney, Agent, or Firm*—Hoffman, Wasson & Gitler

[57] ABSTRACT

An enhanced knotless suture anchor assembly having a snag element or recess attached to, or formed in, an anchor assembly, for capturing a looped section of the suture element for enhanced knotless surgical soft tissue reattachment to bone, and an unique method for using a plurality of anchors and attachments to provide such attachment or reattachment.

6 Claims, 3 Drawing Sheets

PROCESS FOR ATTACHING TISSUE TO BONE USING A CAPTURED-LOOP KNOTLESS SUTURE ANCHOR ASSEMBLY

This application is a continuation-in-part of application Ser. No. 08/792,738 filed on Jan. 31, 1997 U.S. Pat. No. 5,709,708.

BACKGROUND OF THE INVENTION

1. Field of the Invention

The present invention relates to a process and device or assembly for use in tissue repair. More particularly, the assembly is an enhanced device that enables the attachment together or repair of portions of biological tissue, such as tendons or ligaments, on a bone surface. Such device or assembly is used in a unique way with unique attachments to reattach or attach tissue to bone.

2. Description of the Background Art

Soft tissues, such as tendons and ligaments, generally are attached to bone by small collagenous fibers. These connections are strong but permit the tendons and ligaments to be flexible. When a tissue is torn away from the bone and requires repair, a surgeon is often required to repair the detached soft tissue with sutures which are passed through bone tunnels and tied. A number of devices have been developed for securing a ligament or tendon to a bone mass. These devices can be used in place of bone tunneling techniques. These attachment devices are usually inserted through extensive surgical incisions and, in some circumstances, by arthroscopic surgical techniques. The use of bone tunnels for repair can be difficult and generally require large open incisions. Recently, through the advent of endoscopic surgery, where the surgeon looks into a joint cavity with a telescope, there has been a trend to repair soft tissues back to bone through small incisions called portals. The unique knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as protheses, to bone. A suture anchor is a device which utilizes small anchors with suture materials attached thereto. A device, such as a screw, is inserted into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during endoscopic surgery and sometimes even in conventional open surgery.

One example of a suture anchor assembly is disclosed in U.S. Pat. No. 5,370,662, wherein an anchor assembly includes a pre-threaded suture positioned at its posterior. First the anchor is inserted into the bone mass. The attached suture is then passed through the tissue for reattachment. The surgeon is required to tie a knot with the suture to complete the surgical process. Some suture anchors can be passed through the soft tissue first and then into the bone. Most suture anchors need to be inserted into the bone first. Only after this has been accomplished can the sutures be passed through the soft tissue. Alternatives to this procedure include non-suture soft tissue anchor systems. A few of these systems, such as those disclosed in U.S. Pat. Nos. 5,013,316 and 4,532,926, can be used arthroscopically but fixation with these devices may not be as secure as that achieved with sutures. Only a few points of fixation are possible with the non-suture type anchor since the device is relatively large. Therefore suture devices are more favorable. This type of non-suture staple device is disadvantageous in that it has been known to crack the bone during deployment, or accidentally transect the object being attached to the bone. In addition, the device itself has been known to crack or break during or after deployment.

U.S. Pat. Nos. 5,037,422; 5,224,946; and 5,236,445 all disclose bone anchor configurations for attaching sutures within openings formed in bones during joint reconstructive surgery and endoscopic surgical procedures. With all these intricate procedures, the suture itself must be inserted through a tissue mass and tied with a surgical knot to repair the soft tissue to bone.

It is an object of the present invention to provide a knotless suture anchor assembly which is easy to use and install.

Another object of the present invention is to provide a suture anchor assembly which allows for secure attachment of soft tissue to a bone mass without the use or requirement of tying a knot.

Still another object of the present invention is to provide a suture anchor assembly which is compact and allows a surgeon to easily guide the anchor means into the bone mass, or anchoring sleeve if desired, to enhance the security of the repair.

Yet another object of the present invention is to provide a process whereby a plurality of knotless suture anchor assemblies can be used to effectively attach or reattach tissue to bone.

Further, another object of the present invention is a mechanism for producing incisions or cuts in tissue for performing reattachment or attachment of tissue to bone using the novel anchor assemblies.

A primary feature of the present invention is to provide a unique snag-type or capture means which is provided to facilitate engagement of the anchor means with a continuous suture loop, for drawing soft tissue to the bone mass, once the anchor means is deposited directly in the bone or in a hollow anchoring sleeve.

SUMMARY OF THE INVENTION

In accordance with the above objects, the present invention is a process of using a plurality of enhanced knotless suture anchor assemblies for attachment or reattachment of biological soft tissue to bone. The unique enhanced knotless suture anchor assembly includes an anchor means which can either be installed into a bone mass or into a hollow anchoring sleeve which has been installed into a bone mass. The hollow anchoring sleeve or anchor means can have varying shaped exteriors for secure capturing or engagement with a bone mass.

Incorporated by reference are U.S. Pat. Nos. 4,007,743; 4,632,101; 4,721,103; 4,870,957; 4,898,156; 4,946,468; 5,084,050; 5,102,421; 5,141,520; 5,192,303; and 5,207,679, which all illustrate varying exterior structures which may embody the anchor means or anchoring sleeve of the invention.

Further, if desired, the hollow anchoring sleeve can contain a collar on the rear portion or rear side to control the depth of sleeve insertion into the bone and prevent excessive insertion depth. The anchor means of the assembly has a first end or configuration which allows for secure capturing of either the hollow anchoring sleeve or the bone mass and a component for securing the suture element or sliding continuous loop of the suture element. The first end can be pointed or frustoconical in shape. The anchor means can be ribbed, beaded, threaded, or expandable on its exterior surface or further can contain one or more prongs for secure mating with the anchoring sleeve or bone mass.

The anchor means has located thereon unique snag means in the shape of a hook, or other type projection, or a recess cut into the anchor, or a slit cut into an existing opening in the anchor, for engaging a continuous loop portion of the suture element. One particular embodiment provides a recess at the apex of the anchor whereby the suture element can be snagged or captured by the anchor.

The suture element can be attached permanently to the rear end of the anchor means or can be attached in a hole thereon in a continuous loop configuration. The hook portion or projection can be made of the same material as the entire anchor means or a different material, as desired. The anchor means can be inserted during an open procedure, or an endoscopic procedure. In the preferred method, the suture element is first passed through the soft tissue and attached or connected to the snag-type means and subsequent to such steps, the anchor means is then inserted into the bone mass or into the hollowing anchoring sleeve which has been inserted into the bone mass.

Secondly, the anchor means can be directly pierced through the tissue and the continuous loop of the suture element can then be attached to the snag means followed by the engagement of the anchor means to the bone mass or hollow anchoring sleeve.

Thirdly, the novel suturing technique utilizing a plurality of capture-loop anchors. The first anchor is pressed or inserted into the bone. The suture loop on the first anchor is then passed through the tissue and is passed back through the tissue a second time at a different location. The loop end of the first assembly is then captured by the snag means or recession in a second anchor and fastened into the bone at a second location, providing a mattress type stitch repair. If desired, the loop of the second suture element can then be fed through the tissue at a third location and then back through the tissue at a fourth location. The suture loop of the second anchor assembly is then captured by a snag means or recession of a third anchor and drawn tight into engagement with the bone producing a second mattress type stitch repair.

The incisions, cuts or passages in the tissue can be accomplished by using a needle and suture loop attachment assembly which has been added to the knotless suture anchor assembly. Upon capture of the first anchor suture loop assembly by a second anchor and after inserting same into bone mass, the needle and suture loop attachment assembly is cut away and discarded. This assembly facilitates the method of stitching and reattachment.

Numerous other features of various embodiments of the enhanced knotless suture anchor assembly will be apparent from the following detailed description and the accompanying drawings.

DETAILED DESCRIPTION OF THE PRESENT INVENTION

Figure 1:
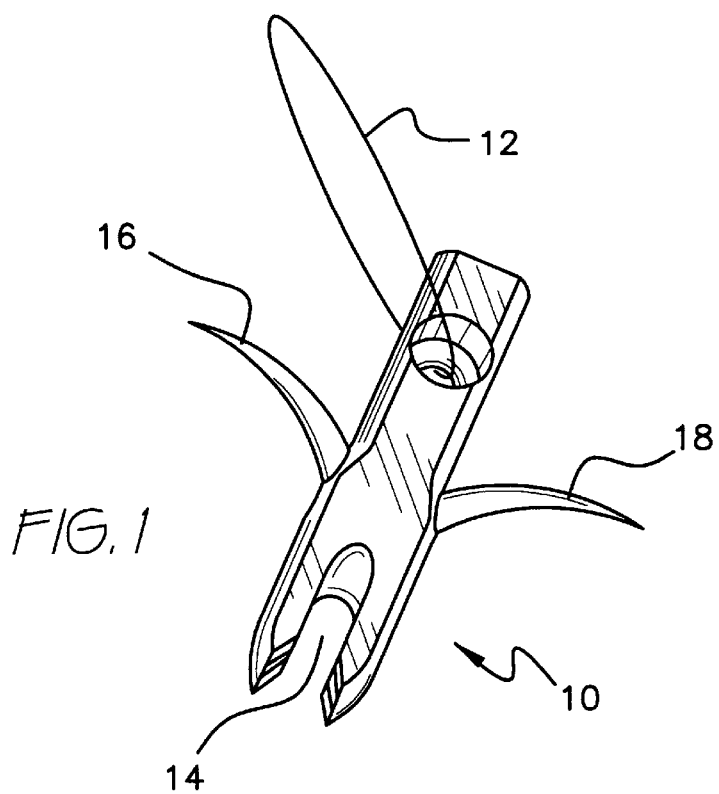
FIG. 1 is a perspective view of an anchor assembly with a continuous loop suture element and a snag recess.

Referring to FIG. 1, the enhanced knotless suture anchor assembly of the present invention contains an anchor means 10, a suture element 12 and a snag means 14. The anchor means in the figure also contains prongs 16 and 18 which facilitate the attachment of the anchor means 10 to a bone mass. The device can also contain, or be configured with, umbrella spokes, it can contain threads, be expandable, or have any other type of engaging features on its exterior for secure attachment with a bone mass. All of these exterior attachment features are known to the industry and incorporated herein by reference.

In all possible embodiments, either the anchor means or the suture element can be passed through the tissue first and then the loop of the suture element is engaged into the recess or onto the projection or hook means thus capturing the suture loop. The anchor is then inserted into either a hollow anchoring sleeve or a bone mass thereby approximating the soft tissue to the bone mass. It is also within the contemplation of the present invention to configure the anchor means such as is disclosed by U.S. Pat. Nos. 4,632,101; 4,721,103; 4,898,156; 5,207,679; 4,946,468; and 5,192,303. A good depiction of the various configuration can be seen in applicant's own U.S. Pat. No. 5,569,306. These patents are incorporated by reference and fall within the contemplation of the present invention for methods or means for anchoring the anchor means or hollow anchoring sleeve to a bone mass.

Figure 2:
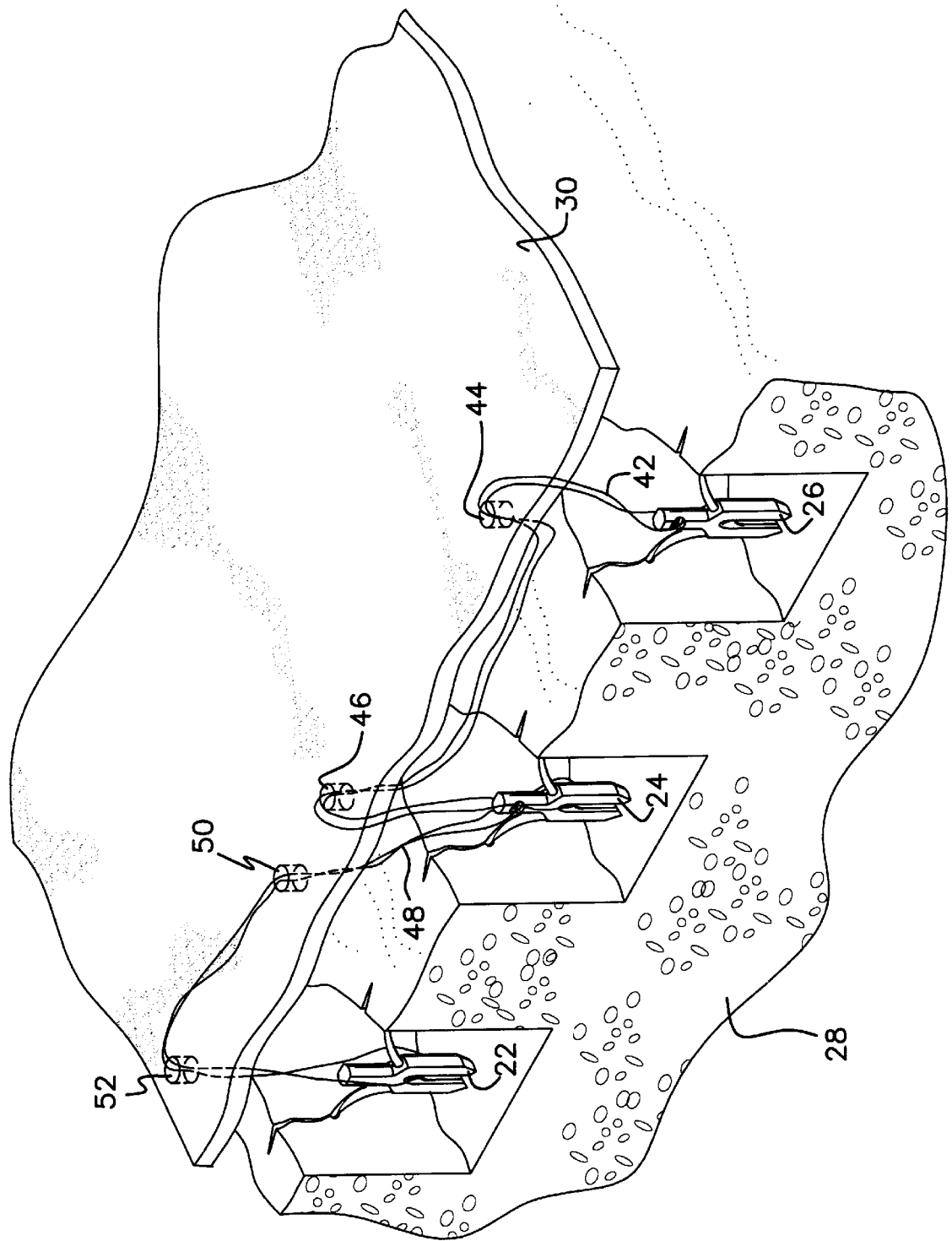
FIG. 2 illustrates a procedure for attachment of tissue to bone mass.

FIG. 2 depicts an unique technique wherein a plurality of captured loop anchor assemblies 22, 24 and 26 are inserted into a bone mass 28 for drawing a tissue 30 into secure engagement therewith. In the procedure or technique, a first anchor assembly 26 is inserted into the bone mass 28. The suture loop element 42 is then passed through the tissue 30 creating a passage 44 in the tissue 30. Conversely the anchor 26 can be passed directly through the tissue forming the passage 44. The suture element 42 formed in the shape of a loop is passed through a second location in the tissue 30 creating a passage 46. Once the suture loop 42 has been passed through passage 46 it is captured or snagged by a second captured loop knotless suture anchor assembly 24 and pressed into the bone mass 28. This completes the repair with a mattress type stitch configuration. If desired, a suture loop element 48 of the second anchor assembly 24 can be passed through the tissue at a third location forming a passage 50. Conversely, the second anchor means can be passed directly through the tissue 30 creating the third passage 50. The suture loop element 48 is then passed through the tissue of a fourth location forming a fourth passage 52. The loop element 48 is then captured by a third anchor assembly 22 and pressed into the bone mass 28. This procedure can be repeated by as many anchors as is required to produce a complete attachment. The passages or incisions can be placed at any desired interval.

Figure 3:
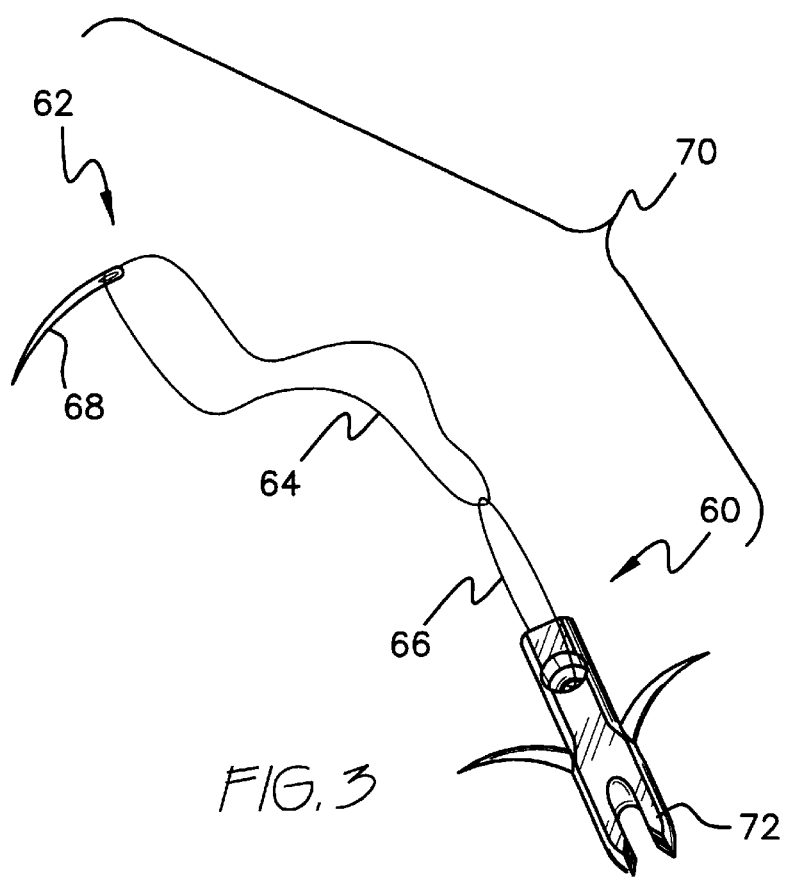
FIG. 3 is a perspective view of an anchor assembly with a needle and suture loop attachment assembly.

FIG. 3 depicts an anchor assembly 60, of the capture type, which contains a needle and suture loop attachment assembly. The assembly contains a suture loop 64 which is looped through the suture loop 66 of the anchor assembly and a needle 68 which can be utilized to produce the passages or incisions by piercing of the tissue.

The process of tissue repair is enhanced by the additional assembly. The procedure can begin with an overall repair assembly 70. The anchor 72 is first inserted into a bone mass. The needle 68 is then passed through a tissue to be attached and the needle suture 64 and the anchor assembly suture loop 66 is pulled through the passage formed therein. These two steps can be reversed and, if desired, the needle 68 can be first passed through the tissue. This is followed by insertion of the anchor 72 into the bone mass. FIG. 2 illustrates how a suture loop 42 of the anchor assembly is pulled through an incision or passage 44. The needle and suture loop attachment assembly is then fed through the tissue at a second location (See incision or passage 46 of FIG. 2). The needle 68 is pulled and the anchor assembly suture loop 66 is then fed through the second passage. The first anchor means 26 of the assembly has already been inserted into the bone mass and the needle 68 is pulled taught. A second anchor 24 (See FIG. 2) captures the suture loop of the first anchor assembly and at such time the needle and suture loop attachment assembly 62 is cut away and discarded. The second anchor assembly also can be provided with a needle and suture loop attachment for a repeat of the technique.

In many situations throughout the discussion above, the terminology secure attachment of soft tissue to bone has been used. Such terminology refers to the attachment or reattachment of tissue to a bone mass through the insertion of an anchor means into the bone mass or a hollow anchoring sleeve. In the one situation, the anchor means can seat into the hollow anchoring sleeve in a one step mating procedure or be inserted and ratcheted down in a step wise fashion into the sleeve. In the second situation, the anchor means will be directly inserted into the bone mass and ratcheted down drawing the tissue to the bone mass as well. In addition to the shapes illustrated for the snag means, such can take the form of anything which would allow the continuous loop portion of the suture to be captured by the hook, projection, slit or recess in the anchor means. The suture element can be made up us a known suture material, or it can be made of polymer materials, or can be formed of bioabsorbable material such as a polylactide polymer.

Figure 4:
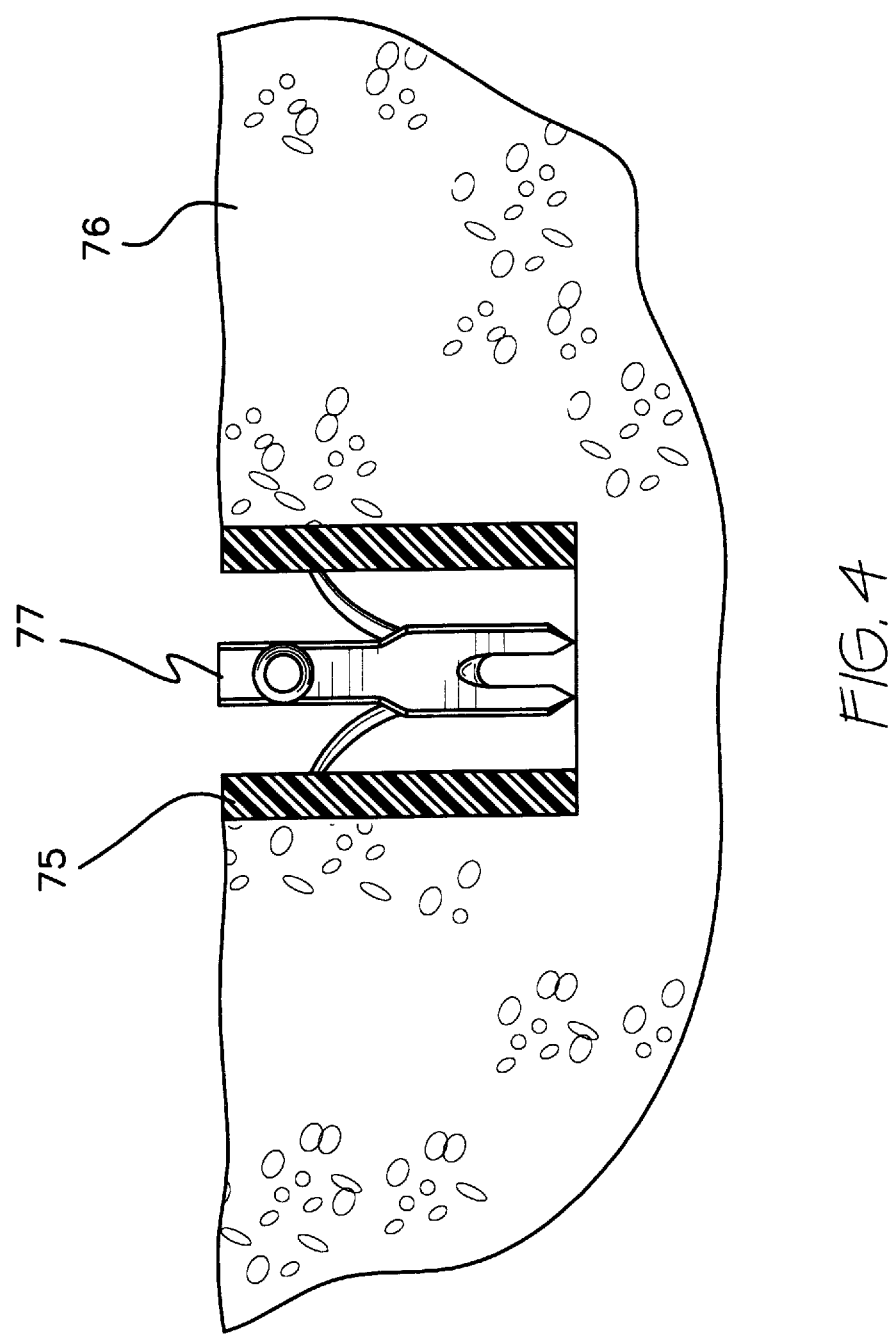
FIG. 4 is a cross sectional view of an anchor assembly in a sleeve or collar in the bone mass.

As described by prior U.S. patents issued to the Applicant, a sleeve or collar 75, see FIG. 4, can first be inserted into the bone mass 76 by various techniques. The sleeve 75 can serve as a mechanism to support the anchor means 77 and allow ratcheting into the bone mass 76 for secure attachment.

While a preferred embodiment of the invention is illustrated, it should be understood that the present disclosure is made by way of example and that variations to the structure shown and its use are possible within the scope of this disclosure without departing from the subject matter coming within the scope of the claims.

What is claimed is:

1. A method for attachment of tissue to bone mass utilizing a plurality of anchor assemblies having a suture capture mechanism and a continuous loop suture element comprising the steps of:
   a) installing an anchor means of a first anchor assembly into said bone mass;
   b) passing a first suture loop element of said first anchor assembly through said tissue to form a passage:
   c) passing said first suture loop element through a tissue at a second location to form a second passage; and
   d) capturing said first suture loop element with a capture means of a second anchor assembly and inserting said second anchor assembly into said bone mass.

2. The method of claim 1, further comprising the steps of:
   e) passing a suture loop element of said second anchor assembly through a third passage in said tissue;
   f) passing said suture element of said second anchor assembly through a fourth passage in said tissue; and
   g) capturing said suture element of said second anchor assembly with a capture means of a third anchor assembly and inserting said third anchor assembly into said bone mass.

3. The method of claim 1, wherein said first anchor assembly includes a needle and suture loop attachment assembly, wherein said suture loop of said attachment assembly is entwined with said first suture loop element of said first anchor assembly.

4. The method of claim 3, further comprising the steps of making said first and second passages in said tissue with said needle of said needle and suture loop attachment assembly.

5. The method of claim 1, wherein prior to installation of said first anchor assembly into said bone mass, a sleeve is installed into said bone mass for holding said anchor assembly in place.

6. A method for attachment of tissue to bone mass utilizing a plurality of anchor assemblies having a suture capture mechanism and a continuous loop suture element comprising the steps of:
   a) passing an anchor means of a first anchor assembly through said tissue and installing said anchor means into said bone mass;
   b) passing a first suture loop of said first anchor assembly through said tissue at a second location; and
   c) capturing said first suture loop element with a capture means of a second anchor assembly and inserting said second anchor assembly into said bone mass.

* * * * *